(12) United States Patent
Thomas et al.

(10) Patent No.: US 6,342,657 B1
(45) Date of Patent: Jan. 29, 2002

(54) SEED SPECIFIC PROMOTERS

(75) Inventors: Terry L. Thomas; Tzung-Fu Hsieh, both of College Station, TX (US)

(73) Assignee: Rhone-Poulenc Agro, Lyons (FR)

( * ) Notice: Subject to any disclaimer, the term of this patent is extended or adjusted under 35 U.S.C. 154(b) by 0 days.

(21) Appl. No.: 09/306,060

(22) Filed: May 6, 1999

(51) Int. Cl.⁷ .......................... C12N 5/04; C12N 15/82; C12N 15/90; A01H 5/00; A01H 5/10
(52) U.S. Cl. .................. 800/287; 435/69.1; 435/320.1; 435/419; 435/468; 435/471; 536/24.1; 800/281; 800/298; 800/306; 800/312; 800/314; 800/320.1; 800/322
(58) Field of Search .......................... 435/69.1, 320.1, 435/410, 412, 415, 416, 414, 419, 468; 536/23.6, 24.1; 800/278, 281, 286, 287, 295, 298, 306, 312, 314, 317.3, 320.1, 322

(56) References Cited

FOREIGN PATENT DOCUMENTS

| WO | WO 98/45461 | 10/1998 | ........... C12N/15/82 |
|---|---|---|---|
| WO | WO 99/20775 | 4/1999 | ........... C12N/15/82 |

OTHER PUBLICATIONS

Baumlein et al, Mol. Gen. Genet., vol. 225, pp. 459–467, 1991.*

Kerstetter, R., et al. (1994) "Sequence Analysis and Expression Patterns Divide the Maize knotted1-like Homeobox Genes into Two Classes" *The Plant Cell* 6: 1877–1887.

Long, J., et al. (1996) "A member of the knotted class of homeodomain proteins encoded by the STM gene of Arabidopsis" *Nature* 379: 66–69.

Cartea, M. E., et al. (1998) "Comparison of sense and antisense methodologies for modifying the fatty acid composition of Arabidopsis thaliana oilseed " *Plant Science 136*: 181–194.

Odell, J., et al. (1994) "Seed-Specific Gene Activation Mediated by the Cre/lox Site-Specific Recombination System" *Plant Physiol 106*: 447–458.

* cited by examiner

*Primary Examiner*—Gary Benzion
*Assistant Examiner*—Ashwin Mehta
(74) *Attorney, Agent, or Firm*—Scully, Scott, Murphy & Presser

(57) ABSTRACT

The present invention is directed to isolated promoter sequences from seed-specific genes, such as KNAT411. When operably linked to either the coding sequence of a heterologous gene or a sequence complementary to a native plant gene, the subject promoters direct expression of the coding sequence or complementary sequence in a plant seed, including the early embryo. The promoter sequences are useful in expression cassettes and expression vectors for the transformation of plants. Also provided are methods of directing seed-specific expression of a gene or sequence complementary to a native plant gene by introducing into a plant cell an isolated nucleic acid comprising a subject promoter operably linked to said gene or complementary sequence. Methods for activating a site-specific recombination system in the early embryo of a seed by transforming a plant with an expression cassette comprising a subject promoter operably linked to a recombinase gene are also provided.

60 Claims, 9 Drawing Sheets

(3 of 9 Drawing Sheet(s) Filed in Color)

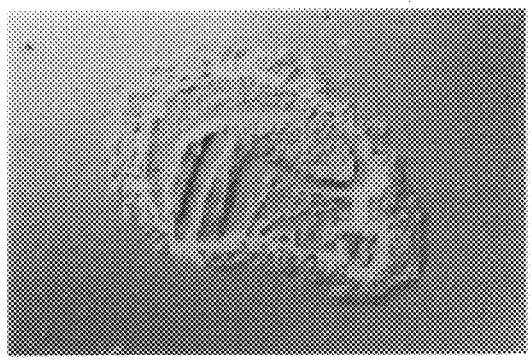 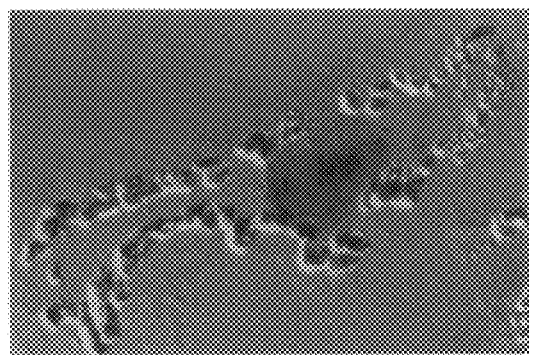
Figure 2A        Figure 2B
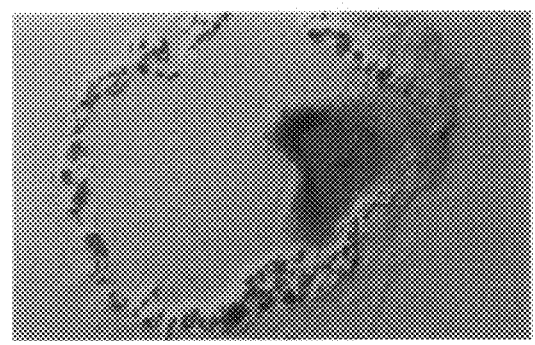 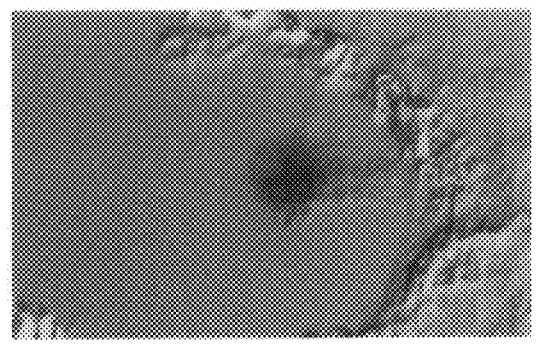
Figure 2C        Figure 2D

```
-1679    gcaacatatgcaacttacaacgaccaaggattccattgttatgatgaaatatatttagttttttgtaattaattgcagt
-1600  ttttttttgcaaaaacttaagactacttggatggctattggctccaatatgccaagccggagaaaaccagaagattta
-1520  agaatatattttttaaacgatgaagtgaaaaataattttttaacgtccaacatgtatgttcagaagatttgtaattc
-1440  tgaacggaactattacatgacgttacaaaaaaccatgccacaagagtatccggacttaacacgtttcacaacacatcaa
-1360  tttttttttttttcagtttttatgatatttctgaaattctagctaaaaatatagttagtatatatcatcaaatatcaa
-1280  ctattgtttgtgtactacatcagatgtatcctatatttcatatcaaactaggaaaaatatgaaagcattttatatctatcaaataactg
-1200  caattaaattatcagagtgttactgttcgttttaaggttatatgactaagaaatggtgcattaaagctgtatcacattttgtcc
-1120  aaaaaattaaactgtatcactattctatactattaaaatagtattttaaactaggtgttaatactatttgttcttaccaaaag
-1040  aagaaaacaaaattttaagttgggaagatatttttattttcctcattctttttcaaaatttc
-960   tagaggattaggtgtgtctaccggtcctgtcgttaaagtgggaagatattttattttcctcattctttttcaaaatttc
-880   aactaatttttaagttttgatcacttgttgtcacttattagttcacgagaaggaaaacaaaaatgttttt
-800   aatttttatttttttacattttatatactattagttatcatgttatgttttgtaaagcacgttgttaacgtgc
-720   acttttttcataacttacgtcaaggtaattcagattaattctagttttcagtcttttcgattgaaacaatcaacgtccgtgtttgtattca
-640   tctagactaagtaatctcagattaattctagttttcagtcttttcgattgaaacaatcaacgtccgtgtttgtattca
-560   catatctgataaaataataacttacaagaaatttttattttttgaaatggaattattgaacgatattgaacgattttgtt
-480   ctgtataaaataataacttacaagaaatttttattttttgaaatggaattattgaacgatattgaacgattttgtt
-400   gaaattgtcgtttgaaaaaaatatgtatggcggaccagacccgtgtataaatgatcaaaaaa
-320   tattttttgaagacaaaaatatcatgtatggcggaccagacccgtgtataaaagaattaaaggggaaag
-240   aaataagacagcagctttatataggtttgatttcatctgacaattctgcctctctctttcttctaatcat
-160   aaatcaggacagcagctttatataggtttgatttcatctgacaattctgcctctctctttcttctaatcat
-80    acgaacacaatctgcttcaagaattaggggttttgatcagacacaaaagtatctctctccgtagttttgtcaaggtt
  1    ATG
```

Figure 4A

SEQUENCE LISTING

<160> NUMBER OF SEQ ID NOS: 1

<210> SEQ ID NO 1
<211> LENGTH: 1679
<212> TYPE: DNA
<213> ORGANISM: Arabidopsis thaliana

<400> SEQUENCE: 1

```
gcaacatatg caattacaac gaccaaggat tccattgtta tgatgaaata ttattttagt      60
ttttgtaatt aattgcagtt ttttttttgc aaaaacttaa gactacttgg atggctattg    120
gctccaatat gccaagccgg aggaaaacca gaagatttaa gaatatattt ttttaaacga    180
tgaagtggaa aaataatttt tttaacgccc aacatgtatg ttcagaagat ttgtaattct    240
gaacggaact attacatgac gttacaaaaa accatgccac aagagtatcc ggacttaaca    300
```

-continued

```
acgtttcaca acacatcaat ttttttttt tcagttttat ggatatttct gaaattctag      360
ctaaaaacta ttagtatata ttaaagttca tatatcaaac tattgtttgt gtactatata     420
aacttcatat caaactagga aaaatatgaa agcatttta tatctatcaa ataatactgc      480
aattaaatta tcagagtgtt actgttttaa ggttatatga ctaagaaatg gtgcattaaa    540
gctgtatcac attttgtcca aaaaaattaa actgtatcac gtaattgact atttaatatt    600
ttaaaagaat aactaattat atttgttctt taccaaaaga agaaaacaaa tatactatat    660
ttctatacta ttaaatagta ttatcaatta ggtgttaata ctatttgtta agtgggcgtt    720
agaggattag gtgtgtctac cggtcctgtc gttaaaggtg ggaagatatt ttattttcct    780 cattctttt caaaattca actaatttt aagttcaagt tgttgatcac ttattaggtc      840
ttaaatcatt gtcacgagaa ggaaaacaaa aatgtttta atttttattt ttattttaca    900
ttttatatac gtacatatac acgtatttat gattttgta aagcacgttg ttaacgtgca    960 ctttttcat aactttacgt caaggtatat actatatc agcatattgt ggaatcaaac     1020
atatatatag tagcagtttt ctagactaaa gtaattcaga ttaattgtaa agataacaat   1080
caccgtataa aacaatcaac gtccgtgtgt ttgtattcac atatctgatg aaaattagta   1140
attctagttt tcagtctttc gattaacaat acaaaattat actttctata tgatttaatc   1200
tgtataaaaa taataactta caaaataaat tttagttagt gttttccagc atgaaaataa   1260
gatattgaac gatttgttg aaattgttcg tttgattttt tattttattt ttgaaagtga    1320
aatggaatta tgtttcagac ttaaaatgat ccaaaaaaat atttttttga aaaaatatgt   1380
atggtatggc ggaccagacc cgtgtataat aaacattgtt ttaaatgtat tttatatata   1440
aataagacaa aataatctat aaaacaaata atgtatattt ttagaaaaga atggagtgaa   1500
aaacaattaa aggggaaaga aatcaggaca gctttatata ggttgatttc atctgacaat   1560
tctctctctc tctctctctc tctctctttt tctaatcata cgaacacaat ctgcttcaag   1620
aattagggtt ttgatcagac acaaaaaagt atctctctcc gtagttttgt gtcaaggtt    1679
```

SEED SPECIFIC PROMOTERS

BACKGROUND OF THE INVENTION

Promoter analysis of seed-specific genes has a rich history (reviewed in Goldberg et al. (1989) *Cell, 56; 149–160*; Thomas (1993) *Plant Cell*, 5; 1401–1410). This stems from the observation that no plant gene is more tightly regulated in terms of spatial expression than those encoding seed storage proteins. Many seed storage protein genes have been cloned from diverse plant species, and their promoters have been analyzed in detail (Thomas, 1993). In these experiments promoter elements, which constitute the 5'-upstream regulatory regions, were functionally defined by their ability to confer seed-specific expression of the bacterial β-glucuronidase (GUS) reporter gene in transgenic plants (Bogue et al. (1980) *Mol. Gen. Genet.*, 222; 49–57; Bustos et al. (1989) *Plant Cell*, 1; 839–853). Results of this work initiated efforts to functionally define cis-elements in the promoters of these genes that are critical for conferring seed-specific expression.

Later experiments involved construction of deletion mutants consisting of target promoters fused to the GUS-reporter gene. Analysis of these constructs in transgenic plants allowed researchers to define regions within each promoter that are critical to its overall regulation (Bustos et al. (1991) *EMBO J.*, 10; 1469–1479; Chung (1995) *Ph.D. Dissertation, Texas A&M University*; Nunberg et al. (1994) *Plant Cell*, 6; 473–486). A general conclusion from this work is that the promoter proximal region contributes primarily to the gene's tissue specificity with more distal regions being responsible for modulating expression levels (Thomas, 1993). In addition to this, several groups have identified and characterized specific cis-regulatory elements, in both the promoter proximal region (PPR) and more distal regions, which interact with DNA binding proteins (Bustos et al., 1989; Chung, 1996; Jordano et al. (1989) *Plant Cell*, 1; 855–866; Nunberg et al., 1994). The functional significance of these regulatory elements varies from gene to gene.

In some cases, cis-regulatory elements have been mapped and the trans-acting factors which confer functionality have been cloned. For example, elements that allow the wheat EM-gene to respond to the plant hormone abcisisic acid (ABA) have been defined. This work led to the identification of a DNA binding protein which mediates this response (Guiltinan et al. (1990) *Science*, 250; 267–271; Marcotte et al. (1989) *Plant Cell*, 1; 969–976). Putative ABA responsive elements have also been mapped in the sunflower helianthinin promoter HaG3-D and the carrot Dc3 promoter (Chung, 1995; Nunberg et al., 1994). Alone these elements act as positive elements in response to ABA. Regulation is restricted to the embryo, however, in the presence of each gene's promoter proximal region (Thomas, 1993).

Despite considerable effort, the cis-regulatory elements which contribute to a promoter's seed-specificity remain elusive (Chung, 1996; Li (1995) *Ph.D. Dissertation, Texas A&M University*). Recent work on the carrot Dc3 promoter proximal region has identified two bZIP genes that functionally interact with critical cis-elements (Kim et al. (1997) *Plant J.*, 11; 1237–1251). This work has increased the understanding of seed-specific gene expression but it has also revealed that seed-specific gene regulation is complex.

In *Arabidopsis thaliana*, the promoters driving the expression of four members of the 2S albumin gene family have been analyzed in detail. The data indicate that each promoter is capable of conferring seed specific expression of a reporter gene in transgenic plants. Each promoter, however, confers slightly different spatial accumulation of the reporter in the developing seed. Thus, each family member contributes to the overall accumulation of the 2S albumins in the developing embryo. This is not unusual behavior for small gene families in plants (Lam et al. (1995) *Plant Cell*, 7; 887–898; Conceicao et al. (1994) *Plant J.*, 5; 493–505; Sjödahl et al. (1993) *Plant Mol. Biol.*, 23; 1165–1176; Pang et al. (1988) *Plant Mol. Biol.*, 11; 805–820). In such cases, each member is capable of functionally complementing the others. The expression of each member is under different regulatory control leading to unique expression patterns. This appears to be a widespread gene regulatory mechanism in plants.

There is substantial interest in identification and isolation of regulatory elements for use in manipulating expression of both native and heterologous genes in plant seeds. For example, well-defined seed specific regulatory elements are useful in manipulating fatty acid synthesis or lipid metabolism genes in plant seeds. Other important agronomic traits such as herbicide and pesticide resistance, and drought tolerance may also be altered in the plant seed by transforming plants with appropriate heterologous genes under the control of well-defined seed-specific promoters and cis regulatory elements.

The present invention provides regulatory sequences which direct seed-specific expression beginning with the early embryo and include a promoter from a seed-specific gene designated KNAT411. The subject promoters are active at a much earlier stage in embryo development than other known seed-specific promoters. The regulatory sequences may be used with any native or heterologous gene or portion thereof for expression of a corresponding gene product in a plant seed.

SUMMARY OF THE INVENTION

The present invention is directed to isolated nucleic acids comprising promoters which direct seed-specific expression beginning in the early embryo. The subject promoters hybridize under stringent hybridization conditions to a promoter isolated from Arabidopsis, designated the KNAT411 promoter, which promoter has the nucleotide sequence as set forth in SEQ ID NO:1.

The present invention is also directed to an isolated nucleic acid comprising a KNAT411 promoter which directs seed-specific expression beginning in the early embryo, which KNAT411 promoter has a restriction map as depicted in FIG. 7.

In other embodiments of the invention, the subject isolated nucleic acids comprise promoters which direct seed-specific expression beginning in the early embryo and have a sequence identity (sequence similarity) of from about 60% to about 65%, or from abut 65% to about 75%, or from about 75% to about 85% when compared to the nucleotide sequence of the KNAT411 promoter as set forth in SEQ ID NO:1. In a preferred embodiment, an isolated nucleic acid comprising a promoter which directs seed specific expression beginning early in the development of the embryo has a sequence identity (sequence similarity) of about 85% to about 90% when compared to the sequence of the KNAT411 promoter as set forth in SEQ ID NO:1. In a most preferred embodiment, an isolated nucleic acid comprising a promoter which directs seed specific expression beginning early in the development of the embryo has a sequence identity embryo has a sequence identity (sequence similarity) of about 90% or greater when compared to the sequence of the KNAT411 promoter as set forth in SEQ ID NO:1.

In a further embodiment, the present invention is directed to an isolated nucleic acid comprising a promoter which directs seed-specific expression beginning early in the development of the seed, which promoter has the nucleotide sequence as set forth in SEQ ID NO:1.

Other embodiments of the present invention include vectors comprising a subject isolated nucleic acid constituting a promoter which directs seed-specific expression beginning in the early embryo including a KNAT411 promoter or portion thereof.

In still another embodiment, the present invention is directed to cells and plants transformed with a vector comprising an isolated nucleic acid constituting a promoter which directs seed-specific expression beginning in the early embryo including a KNAT411 promoter or portion thereof, and the progeny generated from such transformed plants.

In still further embodiments, the present invention provides expression cassettes which comprise an isolated nucleic acid constituting a promoter which directs expression beginning in the early embryo of a seed including a KNAT411 promoter or portion thereof operably linked to a heterologous gene or a nucleic acid encoding a sequence complementary to the native plant gene and vectors containing such expression cassettes.

In still another embodiment, this invention provides a method for directing seed-specific expression in a plant by providing such plant with an isolated nucleic acid constituting a promoter which directs expression beginning in the early embryo including a KNAT411 promoter to effect such seed-specific expression.

The present invention also contemplates expression cassettes which comprise an isolated nucleic acid constituting a promoter which directs expression in the early embryo of a seed including a KNAT411 promoter, operably linked to a recombinase gene such as Cre or FLP (Odell et al. 1994 *Plant Physiol.* 106:447–458 and references therein). Such expression cassettes are useful for inducing site specific recombination in the early plant embryo. Transgenic plants comprising such expression cassettes activate a recombination system early in embryogenesis resulting in the recombination event being fixed in the germline of the plant.

BRIEF DESCRIPTION OF THE DRAWINGS

The file of this patent contains at least one drawing executed in color as determined by the U.S. Pat. and Trademark Office. Copies of this patent with color drawing (s) will be provided by the Patent and Trademark Office upon request and payment of the necessary fees.

FIG. 2A is a photomicrograph showing in situ localization of KNAT411 in an 8-cell stage embryo.

FIG. 2B is a photomicrograph showing in situ localization of the KNAT411 gene in an Arabidopsis heart stage embryo.

FIG. 2C is a photomicrograph showing in situ localization of the KNAT411 gene in a late heart stage Arbidopsis embryo.

FIG. 2D is a photomicrograph showing in situ localization of the KNAT411 gene in a mid-cotyledon stage embryo.

FIG. 4A depicts the nucleotide sequence of a 1.679 kb promoter fragment of the KNAT411 gene which lies immediately upstream of the putative translational start site. The putative TATA box, CAT box sequence and first ATG are bolded.

DETAILED DESCRIPTION OF THE INVENTION

The present invention provides isolated nucleic acid sequences corresponding to promoters which direct seed-specific expression in a plant seed, commencing with the onset of early embryo development. In accordance with the present invention, a subject promoter, when operably linked to either coding sequence of a gene or a sequence complementary to a native plant gene, directs expression of the coding sequence or complementary sequence in a plant seed, including the early embryo.

In one embodiment of the invention, there is provided an isolated nucleic acid sequence corresponding to a promoter from an Arabidopsis seed-specific gene, designated KNAT411, having the nucleotide sequence −1679 to −1 as depicted in FIG. 4A (SEQ ID NO:1).

The promoters of the present invention are useful in the construction of expression cassettes which comprise in the 5' to 3' direction, a promoter which directs seed-specific expression in a plant seed such as the KNAT411 promoter, a heterologous gene or sequence complementary to a native plant gene under control of the promoter and a 3' termination sequence. Such an expression cassette can be incorporated into a variety of autonomously replicating vectors in order to construct an expression vector.

Figure 7:
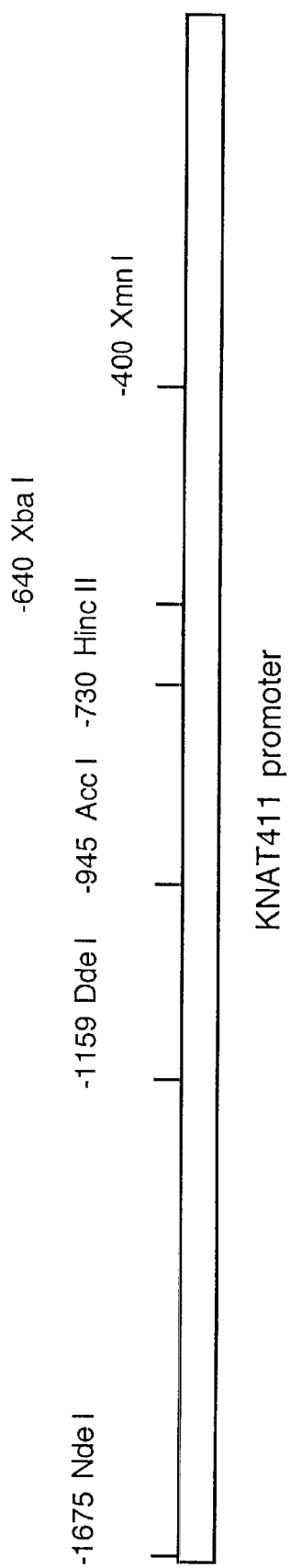
FIG. 7 is a restriction map of the KNAT411 promoter isolated from *Aarabidopsis thaliana*.

The promoter of the KNAT411 gene is herein defined as the approximately 1.6 kb of sequence located directly upstream from the translational start codon (located at position +1 in FIG. 4A). The KNAT411 promoter can also be described in terms of its unique restriction enzyme sites as depicted in the map provided at FIG. 7. Thus, seed-specific promoters having the restriction map depicted in FIG. 7 define a KNAT411 promoter within the scope of the present invention.

The term "seed-specific expression" as used herein, refers to expression in various portions of a plant seed such as the embryo from fertilization to the dry, mature seed.

In one embodiment of the present invention, there is provided a promoter from an Arabidopsis KNAT411 gene. An isolated nucleic acid for a promoter from a KNAT411 gene can be provided as follows. KNAT411 recombinant genomic clones are first isolated by screening a plant genomic DNA library with a cDNA (or a portion thereof) representing KNAT411 mRNA. In order to obtain a cDNA representing KNAT411 mRNA, an oligonucleotide primer may be designed based on the consensus amino acid sequences found in the third helix within the homeodomains of the knotted homeobox gene family. This gene family is described in Kerstetter et al., 1994 *Plant Cell* 6:1877–1887. For example, primer sequences may be designed corresponding to the consensus amino acid sequence: NNWFIN-QRK.

The primer may be used in a PCR reaction and the amplified product cloned and used as a probe to screen an immature seed cDNA library.

Methods considered useful in obtaining genomic recombinant DNA sequences corresponding to the KNAT411 gene of the present by screening a genomic library are provided in Sambrook et al. (1989), *Molecular Cloning: A Laboratory Manual*, Cold Spring Harbor, N.Y., for example, or any of the myriad of laboratory manuals on recombinant DNA technology that are widely available.

To determine nucleotide sequences, a multitude of techniques are available and known to the ordinarily skilled artisan. For example, restriction fragments containing a corresponding KNAT411 gene can be subcloned into the polylinker site of a sequencing vector such as pBluescript (Stratagene). These pBluescript subclones can then be sequenced by the double-stranded dideoxy method (Chen et al. (1985) *DNA*, 4; 165).

In a preferred embodiment of the present invention, the KNAT411 promoter comprises nucleotides –1679 to –1 of FIG. 4A (SEQ ID NO:1).

Modifications to the KNAT411 promoter as set forth in SEQ ID NO:1, which maintain the characteristic property of directing early seed-specific expression, are within the scope of the present invention. Such modifications include insertions, deletions and substitutions of one or more nucleotides.

The subject KNAT411 promoter can be derived from restriction endonuclease or exonuclease digestion of isolated KNAT411 genomic clones. Thus, for example, the known nucleotide or amino acid sequence of the coding region of a gene of the knotted homeobox gene family is aligned to the nucleic acid or deduced amino acid sequence of an isolated seed-specific genomic clone and the 5' flanking sequence (i.e., sequence upstream from the translational start codon of the coding region) of the isolated KNAT411 genomic clone located.

The KNAT411 promoter as set forth in SEQ ID NO:1 (nucleotides –1679 to –1 of FIG. 4A) may be generated from genomic clones having either or both excess 5' flanking sequence or coding sequence by exonuclease III-mediated deletion. This is accomplished by digesting appropriately prepared DNA with exonuclease III (exoIII) and removing aliquots at increasing intervals of time during the digestion. The resulting successively smaller fragments of DNA may be sequenced to determine the exact endpoint of the deletions. There are several commercially available systems which use exonuclease III (exoIII) to create such a deletion series, e.g. Promega Biotech, "Erase-A-Base" system. Alternatively, PCR primers can be defined to allow direct amplification of the subject KNAT411 promoter.

Using the same methodologies, the ordinarily skilled artisan can generate one or more deletion fragments of the KNAT411 promoter as set forth in SEQ ID NO:1. Any and all deletion fragments which comprise a contiguous portion of the nucleotide sequences set forth in SEQ ID NO:1 and which retain the capacity to direct seed-specific expression starting in the early embryo are contemplated by the present invention.

In addition to the Arabidopsis KNAT411 promoter which nucleotide sequence is set forth as –1679 to –1 in FIG. 4A (SEQ ID NO:1), the present invention is directed to other promoter sequences which correspond to the same gene, i.e., a homolog, in other plant species. As defined herein, such related sequences which direct seed-specific expression beginning with early embryogenesis in a plant seed, may be described in terms of their percent homology on a nucleotide level to the nucleotide sequence (–1679 to –1) as set forth in FIG. 4A (SEQ ID NO:1). Alternatively, such related sequences from other plant species may be defined in terms of their ability to hybridize to the KNAT411 promoter fragment under stringent hybridization conditions.

The present invention therefore contemplates nucleic acid sequences hybridizing with the KNAT411 nucleic acid sequence as set forth in FIG. 4A (SEQ ID NO:1) and which differ in one or more positions in comparison with SEQ ID NO:1 so long as such hybridizing sequence corresponds to a promoter which directs seed-specific expression commencing with early embryogenesis in the seed.

By "hybridizing" it is meant that such nucleic acid molecules hybridize under conventional hybridization conditions, preferably under stringent conditions such as described by, e.g., Sambrook (Molecular Cloning; A Laboratory Manual, 2nd Edition, Cold Spring Harbor Laboratory Press, Cold Spring Harbor, N.Y. (1989)). An example of one such stringent hybridization condition is hybridization at 4×SSC at 650° C., followed by a washing in 0.1×SSC at 65° C. for one hour. Alternatively, an exemplary stringent hybridization condition is in 50% formamide, 4×SSC at 42° C.

Promoter sequences of the present invention may also be described in terms of percent homology on a nucleotide level to the nucleotide sequence –1679 to –1 depicted in FIG. 4A (SEQ ID NO:1). There are a number of computer programs that compare and align nucleic acid sequences which one skilled in the art may use for purposes of determining sequence identity (sequence similarity).

Thus, an isolated nucleic acid comprising a promoter which directs seed specific expression beginning early in the development of the embryo has a sequence identity (sequence similarity) of about 60% to about 65% when compared to the nucleotide sequence of the KNAT411 promoter as set forth in SEQ ID NO:1. In a preferred embodiment, an isolated nucleic acid comprising a promoter which directs seed specific expression beginning early in the development of the seed has a sequence identity (sequence similarity) of about 65% to about 75% when compared to the sequence of the KNAT411 promoter as set forth in SEQ ID NO:1.

In a more preferred embodiment, an isolated nucleic acid comprising a promoter which directs seed specific expression beginning early in the development of the embryo has a sequence identity (sequence similarity) of about 75% to about 85% when compared to the sequence of the KNAT411 promoter as set forth in SEQ ID NO:1.

In an even more preferred embodiment, an isolated nucleic acid comprising a promoter which directs seed specific expression early in the development of the seed has a sequence identity (sequence similarity) of about 85% to about 90% when compared to the sequence of the KNAT411 promoter as set forth in SEQ ID NO:1.

In a most preferred embodiment, an isolated nucleic acid comprising a promoter which directs seed specific expression early in the development of the seed has a sequence identity (sequence similarity) of about 90% or greater when compared to the sequence of the KNAT411 promoter as set forth in SEQ ID NO:1.

Sequences similar to a subject promoter can be identified by database searches using the promoter or elements thereof, as the query sequence using the Gapped BLAST algorithm (Altschul et al., 1997 *Nucl. Acids Res.* 25:3389–3402) with the BLOSUM62 Matrix, a gap cost of 11 and persistence cost of 1 per residue and an E value of 10. Two sequences may be compared with either ALIGN (Global alignment) or LALIGN (Local homology alignment) in the FASTA suite of applications (Pearson and Lipman, 1988 *Proc. Nat. Acad. Sci.* 85:2444–24448; Pearson, 1990 *Methods in Enzymology* 183:63–98) with the BLOSUM50 matrix and gap penalties of −16, −4.

Nucleic acid molecules corresponding to promoters of the present invention can be obtained by using the subject 1.679 kb KNAT411 promoter or a portion thereof (including fragments) or complements thereof as a probe and hybridizing with a nucleic acid molecule(s) from any higher plant. Nucleic acid molecules hybridizing probe and hybridizing with a nucleic acid molecule(s) from any higher plant. Nucleic acid molecules hybridizing to the 1.679 kb KNAT411 promoter or a portion thereof can be isolated, e.g., from genomic libraries by techniques well known in the art. Promoter fragments homologous to KNAT411 may also be isolated by applying a nucleic acid amplification technique such as the polymerase chain reaction (PCR) using as primers oligonucleotides derived from sequence set forth in SEQ ID NO:1.

Confirmation of the seed-specificity of the KNAT411 promoter (including modifications or deletion fragments thereof), and promoters from homologous genes which direct seed-specific expression beginning early in embryo development, can be accomplished by construction of transcriptional and/or translational fusions of specific sequences with the coding sequences of a heterologous gene, transfer of the chimeric gene into an appropriate host, and detection of the expression of the heterologous gene. The assay used to detect expression depends upon the nature of the heterologous sequence. For example, reporter genes, exemplified by chloramphenicol acetyl transferase and β-glucuronidase (GUS), are commonly used to assess transcriptional and translational competence of chimeric constructions. Standard assays are available to sensitively detect the reporter enzyme in a transgenic organism.

The β-glucuronidase (GUS) gene is useful as a reporter of promoter activity in transgenic plants because of the high stability of the enzyme in plant cells, the lack of intrinsic β-glucuronidase activity in higher plants and availability of a quantitative fluorimetric assay and a histochemical localization technique. Jefferson et al. (1987b) *EMBO J* 6; 3901–3907 have established standard procedures for biochemical and histochemical detection of GUS activity in plant tissues. Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. The construction of such chimeric genes allows definition of specific regulatory sequences and demonstrates that these sequences can direct expression of heterologous genes in a seed-specific manner.

Another aspect of the invention is directed to expression cassettes (also termed herein "chimeric genes") and expression vectors comprising a promoter which directs seed-specific expression such as a KNAT411 promoter or portion thereof, operably linked to the coding sequence of a heterologous gene such that the regulatory element is capable of controlling expression of the product encoded by the heterologous gene. The heterologous gene can be any gene other than KNAT411. If necessary, additional regulatory elements from genes other than KNAT411 or parts of such elements sufficient to cause expression resulting in production of an effective amount of the polypeptide encoded by the heterologous gene are included in the chimeric constructs.

As used herein, the term "cassette" refers to a nucleotide sequence capable of expressing a particular gene if said gene is inserted so as to be operably linked to one or more regulatory regions present in the nucleotide sequence. Thus, for example, the expression cassette may comprise a heterologous coding sequence which is desired to be expressed in a plant seed. The expression cassettes and expression vectors of the present invention are therefore useful for directing seed-specific expression of any number of heterologous genes.

Accordingly, the present invention provides chimeric genes comprising sequences of a promoter which directs seed-specific expression including the KNAT411 promoter which are operably linked to a sequence encoding a heterologous gene such as a lipid metabolism enzyme. Examples of lipid metabolism genes useful for practicing the present invention include lipid desaturases such as Δ6-desaturases, Δ12-desaturases, Δ15-desaturases and other related desaturases such as stearoyl-ACP desaturases, acyl carrier proteins (ACPs), thioesterases, acetyl transacylases, acetyl-coA carboxylases, ketoacyl-synthases, malonyl transacylases, and elongases. Such lipid metabolism genes have been isolated and characterized from a number of different bacteria and plant species. Their nucleotide coding sequences as well as methods of isolating such coding sequences are disclosed in the published literature and are widely available to those of skill in the art.

In particular, the Δ6-desaturase genes disclosed in U.S. Pat. Nos. 5,552,306 and 5,614,393 and incorporated herein by reference, are contemplated as lipid metabolism genes particularly useful in the practice of the present invention.

Additionally, the present invention provides chimeric genes which express products having recombinase activity. Introduction into a plant cell of a chimeric gene comprising a recombinase gene operably linked to the subject promoter sequences such as the KNAT411 promoter allows for recombination early in embryogenesis. Expression cassettes which comprise the subject promoter such as the KNAT411 promoter operably linked to a recombinase gene such as Cre, FLP, R, and Gin (Odell et al. 1994 *Plant Phys.* 106:447–458) are particularly contemplated. For example, an expression cassette comprising a subject promoter operably linked to the Cre coding region is introduced into either a plant having endogenous loxP (lox) sites surrounding a gene of interest or a plant which has had loxP sites introduced in an earlier transformation event and surrounding a gene of interest.

Such lox sites integrated into the plant genome are recognized and recombined by Cre. Thus for example, the subject seed-specific promoter/Cre expression vectors may be introduced into a plant in order to mediate excision or inversion of a gene of interest surrounded by lox sites, resulting in activation or inactivation of the gene of interest. Examples of genes of interest for the practice of site specific recombination include anonymous genes involved in embryogenesis and seed development or genes of unknown function that are expressed in seed development such as PEI1 (Li and Thomas, 1998 *Plant Cell* 10:383–398) for which stable mutations do not exist. Other genes of interest include lipid desaturase genes or genes coding for branching enzymes in the lipid desaturation pathway.

The chimeric genes of the present invention are constructed by ligating a subject promoter such as the KNAT411 promoter or part thereof, to the coding sequence of a heterologous gene. The juxtaposition of these sequences can be accomplished in a variety of ways. In one embodiment, the order of sequences in a 5' to 3' direction, is a subject promoter such as the KNAT411 promoter and coding sequence for a heterologous gene. In a preferred embodiment, the order of sequences in a 5' to 3' direction is a subject promoter such as the KNAT411 promoter, a coding sequence and a termination sequence which includes a polyadenylation site.

Standard techniques for construction of such chimeric genes are well known to those of ordinary skill in the art and can be found in references such as Sambrook et al.(1989). A variety of strategies are available for ligating fragments of DNA, the choice of which depends on the nature of the termini of the DNA fragments.

The restriction or deletion fragments that contain a subject promoter TATA box are ligated in a forward orientation to a promoterless heterologous gene such as the coding sequence of β-glucuronidase (GUS). The skilled artisan will recognize that the subject promoters and parts thereof, can be provided by other means, for example chemical or enzymatic synthesis.

The 3' end of a heterologous coding sequence is optionally ligated to a termination sequence comprising a polyadenylation site, exemplified by, but not limited to, the nopaline synthase polyadenylation site, or the octopine T-DNA gene 7 polyadenylation site. Alternatively, the polyadenylation site can be provided by the heterologous gene.

The present invention also provides methods of increasing levels of heterologous genes in plant seeds. In accordance with such methods, the subject expression cassettes and expression vectors are introduced into a plant in order to effect expression of a heterologous gene. For example, a method of producing a plant with increased levels of a product of a fatty acid synthesis or lipid metabolism gene is provided by transforming a plant cell with an expression vector comprising a subject promoter such as a KNAT411 promoter or portion thereof, operably linked to a fatty acid synthesis or lipid metabolism gene and regenerating a plant with increased levels of the product of said fatty acid synthesis or lipid metabolism gene.

The present invention also provides a method for activating a site-specific recombination system early in embryogenesis. Site specific recombination systems which function in plants are known to those skilled in the art and are reviewed in Odell and Russell (1994) "Use of site-specific recombination systems in plants. " In J. Paszkowski, ed. *Homologous Recombination in Plants*, Kluwer Academic Publishers, Dordrecht, The Netherlands, pp. 219–270. The disclosure of this publication and of all other publications and patents cited in this application are incorporated herein as if fully set forth.

In accordance with the present invention, the method for activating a site-specific recombination system early in embryogenesis entails introducing into a plant cell a hybrid gene which comprises a subject promoter such as the KNAT411 promoter operably linked to a recombinase gene such as Cre, FLP, R, or Gin (Odell et al. 1994 *Plant Phys.* 106:447–458). In the case of a hybrid gene comprising a subject promoter such as the KNAT411 promoter operably linked to the Cre coding region, such hybrid gene is introduced into a plant having lox sites surrounding a gene of interest. Such lox sites integrated into the plant genome are recognized and recombined by Cre. Thus, Cre-mediated excision or inversion of a gene of interest surrounded by lox sites results in activation or inactivation of the gene of interest. In accordance with the present invention, recombination events using a subject promoter/Cre vector will occur early in embryogenesis. Recombination events will therefore be fixed in the germline of resultant plants.

For example, the subject KNAT411 promoter/Cre hybrid genes may be introduced into a plant in order to activate a gene silenced by surrounding lox sites situated between the gene's promoter and coding region. The subject KNAT411 promoter/Cre hybrid gene may also be used to invert a lox-bounded coding region situated in inverted orientation with respect to its promoter. The subject method also provides for eliminating expression of a gene located between lox sites through excision by Cre under control of a subject promoter such as the KNAT411 promoter. Examples of genes of interest for the practice of site specific recombination include anonymous genes involved in embryogenesis and seed development or genes of unknown function that are expressed in seed development such as PEI1 (Li and Thomas, 1998 *Plant Cell* 10:383–398). Other genes of interest include lipid desaturase genes or genes coding for branching enzymes in the lipid desaturation pathway.

Another aspect of the present invention provides methods of reducing levels of a product of a gene which is native to a plant which comprises transforming a plant cell with an expression vector comprising a subject promoter such as the KNAT411 promoter or part thereof, operably linked to a nucleic acid sequence which is complementary to the native plant gene. In this manner, levels of endogenous product of the native plant gene are reduced through the mechanism known as antisense regulation. Thus, for example, levels of a product of a fatty acid synthesis gene or lipid metabolism gene are reduced by transforming a plant with an expression vector comprising a subject seed-specific promoter or part thereof, operably linked to a nucleic acid sequence which is complementary to a nucleic acid sequence coding for a native fatty acid synthesis or lipid metabolism gene.

The present invention also provides a method of icosuppressing a gene which is native to a plant which comprises transforming a plant cell with an expression vector comprising a subject promoter such as a KNAT411 promoter or part thereof, operably linked to a nucleic acid sequence coding for the native plant gene. In this manner, levels of endogenous product of the native plant gene are reduced through the mechanism known as cosuppression. Thus, for example, levels of a product of a fatty acid synthesis gene or lipid metabolism gene are reduced by transforming a plant with an expression vector comprising a subject promoter or part thereof, operably linked to a nucleic acid sequence coding for a native fatty acid synthesis or lipid metabolism gene native to the plant. Although the exact mechanism of cosuppression is not completely understood, one skilled in the art is familiar with published works reporting the experimental conditions and results associated with cosuppression (Napoli et al. (1990) *The Plant Cell*, 2; 270–289; Van der Krol (1990) *Plant Mol. Biol*, 14; 457–466.)

To provide regulated expression of the heterologous or native genes, plants are transformed with the chimeric gene constructions of the invention. Methods of gene transfer are well known in the art. The chimeric genes can be introduced into plants by leaf disk transformation-regeneration procedure as described by Horsch et al. (1985) *Science*, 227; 1229–1231. Other methods of transformation such as protoplast culture (Horsch et al. (1984) *Science*, 223; 496; DeBlock et al. (1984) *EMBO J.*, 2; 2143; Barton et al. (1983) *Cell*, 32; 1033) can also be used and are within the scope of this invention. In a preferred embodiment, plants are transformed with Agrobacterium-derived vectors such as those described in Klett et al. (1987) *Annu. Rev. Plant Physiol.*, 38; 467. Other well-known methods are available to insert the chimeric genes of the present invention into plant cells. Such alternative methods include biolistic approaches (Klein et al. (1987) *Nature*, 327; 70), electroporation, chemically-induced DNA uptake, and use of viruses or pollen as vectors.

When necessary for the transformation method, the chimeric genes of the present invention can be inserted into a plant transformation vector, e.g. the binary vector described by Bevan (1984) *Nucleic Acids Res.*, 12; 8711–8721. Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors, the tumor inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transfer of sequences bordered by the T-region into the nuclear genome of plants.

Surface-sterilized leaf disks and other susceptible tissues are inoculated with the "disarmed" foreign DNA-containing *A. tumefaciens*, cultured for a number of days, and then transferred to antibiotic-containing medium. Transformed shoots are then selected after rooting in medium containing the appropriate antibiotic, and transferred to soil. Transgenic plants are pollinated and seeds from these plants are collected and grown on antibiotic medium.

Expression of a heterologous or reporter gene in developing seeds, young seedlings and mature plants can be monitored by immunological, histochemical, mRNA expression or activity assays. As discussed herein, the choice of an assay for expression of the chimeric gene depends upon the nature of the heterologous coding region. For example, Northern analysis can be used to assess transcription if appropriate nucleotide probes are available. If antibodies to the polypeptide encoded by the heterologous gene are available, Western analysis and immunohistochemical localization can be used to assess the production and localization of the polypeptide. Depending upon the heterologous gene, appropriate biochemical assays can be used. For example, acetyltransferases are detected by measuring acetylation of a standard substrate. The expression of a lipid desaturase gene can be assayed by analysis of fatty acid methyl esters (FAMES).

Another aspect of the present invention provides transgenic plants or progeny of these plants containing the chimeric genes of the invention. Both monocotyledonous and dicotyledonous plants are contemplated. Plant cells are transformed with the chimeric genes by any of the plant transformation methods described above. The transformed plant cell, usually in the form of a callus culture, leaf disk, explant or whole plant (via the vacuum infiltration method of Bechtold et al. (1993) *C.R. Acad. Sci. Paris*, 316; 1194–1199) is regenerated into a complete transgenic plant by methods well-known to one of ordinary skill in the art (e.g., Horsh et al., 1985). In a preferred embodiment, the transgenic plant is sunflower, soybean, maize, cotton, tobacco, peanut, flax, Arabidopisis, oil seed rape or other Brassica plant. Since progeny of transformed plants inherit the chimeric genes, seeds or cuttings from transformed plants may be used to maintain the transgenic line.

The following examples further illustrate the invention.

EXAMPLE 1

ISOLATION OF THE KNAT411 cDNA
Plant Maintenance and Tissue Preparation

*Arabidopsis thaliana* (Landsberg) plants were grown under continuous illumination in a vermiculite/soil mixture at ambient temperature (22° C.). Siliques were dissected 2 to 5 days after flowering to separate immature seeds from the silique coats. Both tissues were frozen in liquid nitrogen and stored at −85° C. Root tissue was obtained from elongated roots grown in liquid culture. The root cultures were started from 4 to 20 seeds which were surface sterilized with 10% bleach/0.1% SDS, rinsed thoroughly with water, and cultured in Gamborg $B_5$ medium for two weeks. Inflorescences containing initial flower buds and fully opened flowers, and leaves of different sizes were also collected.

RNA Preparation

Total RNA was prepared following a procedure that has been modified from Galau et al. (1981) *J. Biol. Chem.*, 256; 2551–2560 and Crouch et al. (1983) *J. Mol. Appl. Genet.*, 2; 273–283. Briefly, at 0–4° C., tissue was ground to powder in liquid nitrogen and the powder was resuspended in homogenization buffer (0.1 M Tris-HCL (pH 9.0), 0.1 M NaCL, 1 mM EDTA (pH 8.0), 0.5% SDS) at 20 mL buffer per gram of tissue (v/w). This was done at 0–4° C. One-half volume of hot phenol, which had been previously equilibrated with homogenization buffer was then added and the mixture was homogenized using a Brinkman polytron at high speed for one minute. One-half volume of SEVAG (chloroform:isoamyl alcohol in a volume ratio of 24:1) was then added and the mixture was homogenized as before. The aqueous phase was separated by centrifugation at 8000×g for 10 minutes and removed. The phenol/SEVAG extraction was repeated and the aqueous phase was removed. Nucleic acids were precipitated in 0.2 M potassium acetate (pH 6.0) and 2.5 volumes ETOH overnight at −20° C. The homogenate was ethanol precipitated once more followed by lithium chloride and potassium acetate precipitations before a final ethanol precipitation. The RNA was stored as an ethanol precipitate at −90° C. until use. Before using the RNA in enzymatic reactions, the precipitate was washed in cold 70% ethanol followed by a cold 95% ethanol wash and resuspended in TE buffer.

Probe Design and Preparation

A degenerate oligonucleotide primer was designed based on the consensus amino acid sequence NNWFINQRK, found in the third helix within the homeodomains of the knotted homeobox gene family. This gene family is described in Kerstetter et al., (1994) *Plant Cell* 6:1877–1887. The degenerate primer had the following nucleotide sequence where I represents inosine:

5'-AA(C/T) AA(C/T) TTG TT(C/T)
ATI AA(C/T) CA(A/G)(A/C)GI AA-3'

The degenerate primer and the T7 primer that flanks the cDNA cloning site were used in a PCR reaction. PCR was performed using approximately $2.6 \times 10^7$ phage particles from an Arabidopsis immature seed cDNA library (Li and Thomas, 1998 *Plant Cell* 10:383–398) in 3 mM $MgCl_2$, 400 $\mu$M dNTP, 1 $\mu$M each primer and 2.5 unit of Taq DNA polymerase in a final volume of 25 $\mu$l reaction. Amplification was carried out in 35 cycles of 94° C., 1 min; 60°, 4 min; and 72° C., 1 min using a thermal cycler. Sequence analysis revealed that one PCR clone contained an insert that showed high sequence homology to known knotted homeobox genes. The full length KNAT411 cDNA clone was further isolated using this PCR fragment cloned into the PCR cloning vector pT7Blue (Novagen, Madison, Wis.) as a probe to screen the same immature seed cDNA library.

Plaque Hybridization

An *Arabidopsis thaliana* var. Landsberg erecta cDNA library representing immature seeds was constructed following the method of Nuccio et al. (1996) *SAAS Bulletin, Biochem. & Biotech.* 9:23–28; and Li and Thomas (1998). The library was plated on XL1-Blue MRF' cells at a density of 50,000 PFU per plate (150 mM) containing LB media. Plaques were transferred to nitrocellulose membranes as recommended by the manufacturer and hybridized by standard methods (Ausubel et al., 1994). After 4 hours prehybridization in hybridization II buffer (1% crystalline BSA, 1 mM EDTA, 0.5 M $NaHPO_4$ pH 7.2, 7% SDS) at 65° C., the amplified PCR product probe, which had been denatured for ten minutes in boiling water, was added to the same hybridization solution. Hybridization was continued up to 24 hours at 65° C. The filters were washed twice in 0.5% crystalline BSA, 1 mM EDTA, 40 mM $NaHPO_4$, pH 7.2, 5% SDS for 5 minutes each at room temperature, and then three times in 1 mM EDTA, 40 mM $NaHPO_4$, pH 7.2, 1% SDS for 10 minutes each at 65° C. Autoradiographs were exposed for 1 day at -85° C.

Sequence Analysis

Mini-prep plasmid DNA was isolated from hybridized plaques and used as templates in cycle sequencing reactions with the SequiTherme® cycle sequencing kit (Epicenter Technologies, Madison, Wis.). Sequence analysis was done locally with GCG (Devereux et al. (1984) *Nucl. Acids Res.*, 12; 387–395) on a DEC Micro VAXII; database searches were done remotely through NCBI using the BLAST algorithm (Altschul et al. (1990) *J. Mol. Biol.*, 215; 403–410).

RNA Gel Blot Analysis

10 $\mu$g of total RNA from flower, leaf, root, immature seed, and silique without seed were resuspended in 10 $\mu$l loading buffer (48% formamide, 1×MOPS buffer 0.02 M 3-[N-morpholino] propane sulfonic acid, 1 mM EDTA, 5 mM sodium acetate at pH 6.0), 17% formalin, 0.7 mg/ml ethidium bromide, 5.3% glycerol, 5.3% saturated bromophenol blue) and resolved on a 1.2% agarose gel containing 7% formaldehyde in 1×MOPS buffer. RNA was transferred to a nylon filter (Micron Separations Incorporated) in 10×SSC. Blots were hybridized to the KNAT411 full length cDNA probe in 50% deionized formamide, 5×SSPE, 1×Dendhardt's solution, 0.1% SDS, and 100 $\mu$g denatured salmon sperm DNA at 42° C. for 24 hours. The radioactive probe was prepared from the KNAT411 full length cDNA template by the random primer method (Feinberg et al. (1983) *Alan. Biochem.*, 132; 6–13) and had a specific activity greater than $1 \times 10^9$ cpm/$\mu$g. Filters were washed first in 0.6 M NaCl, 0.08 M Tris-HCl, 4 mM EDTA, 12.5 mM phosphate buffer, pH 6.8 and 0.2% SDS at 60° C. for 15 minutes, followed by 0.3 M NaCl, 0.04 M Tris-HCL, 2 mM EDTA, 12.5 mM phosphate buffer, pH 6.8, and 0.2% SDS at 60° C. for 15 minutes, and then 0.15 M NaCl 0.02 M Tris-HCl, 1 mM EDTA, 12.5 mM phosphate buffer, pH 6.8 and 0.2% SDS at 60° C. for 10 minutes. The filters were wrapped in Saran Wrap and autoradiographed.

Figure 1:
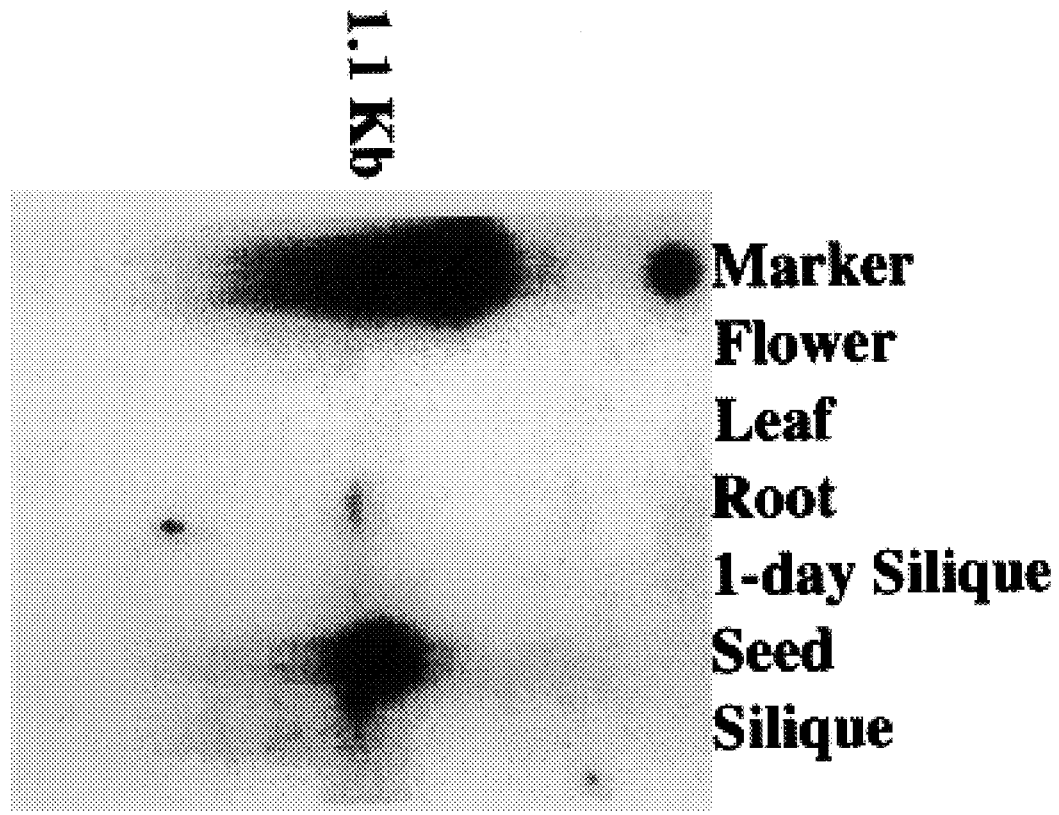
FIG. 1 depicts an autoradiograph of an RNA gel blot probed with a KNAT411 full length cDNA.

RNA gel blot analysis (FIG. 1) indicated that KNAT411 is highly expressed in developing embryos and is expressed at much lower levels in root and silique. Further, KNAT411 is not expressed in leaf or flower tissues under the hybridization conditions described above.

EXAMPLE 2

CHARACTERIZATION OF KNAT411 BY QUANTITATIVE RNA GEL BLOT ANALYSIS

RNA Gel Blot Analysis

The developmental profile of KNAT411 expression was determined by quantitative RNA gel blot analysis using a Fuji BAS-2000 phosphoimager.

*Arabidopsis thaliana* (Landsberg) growth conditions and tissue preparation were as described in Example 1. RNA was also prepared as described in Example 1. Tissue representing globular-heart (1–3 day post flowering), heart to torpedo (3–5 day post flowering), torpedo to early cotyledon (5–7 day) post flowering), early cotyledon to late cotyledon (7–13 day post flowering) stage siliques was collected and stored at -90° C. Dry seeds, floral and leaf tissue were also collected. Ten micrograms of total RNA were resuspended in 10 $\mu$l loading buffer (48% formamide, 1×MOPS buffer 0.02 M 3-[N-morpholino] propane sulfonic acid, 1 mM EDTA, 5 mM sodium acetate at pH 6.0), 17% formalin, 0.7 mg/ml ethidium bromide, 5.3% glycerol, 5.3% saturated bromophenol blue) and resolved on a 1.2% agarose gel containing 7% formaldehyde in 1×MOPS buffer. RNA was transferred to a nylon filter (Micron Separations Incorporated, Westboro Mass.) in 10×SSC. Blots were hybridized with probes prepared from gel purified cDNA inserts in 50% deionized formamide, 5×SSPE, 1×Denhardt's solution, 0.1% SDS, and 100 $\mu$g denatured salmon sperm DNA at 42° C. for 24 hours.

Radioactive probes were prepared from cDNA templates representing the KNAT411 gene and the Arabidopsis 12S seed storage protein gene (Pang et al. 1988 *Plant Mol. Biol.* 11:805–820) by the random priming method (Feinberg et al., 1983) and each had a specific activity of greater than $1 \times 10^9$ cpm/$\mu$g. Filters were washed first in 0.6M NaCl, 0.08 M Tris-HCl, 4 mM EDTA, 12.5 mM phosphate buffer, pH 6.8, and 0.2% SDS at 60° C. for 15 minutes, and then 0.3 M NaCl, 0.04 M Tris-HCl, 2 mM EDTA, 12.5 mM phosphate buffer, pH 6.8, and 0.2% SDS at 60° C. for 15 minutes, followed by 0.15 M NaCl, 0.02 M Tris-HCl, 1 mM EDTA, 12.5 mM phosphate buffer, pH 6.8, and 0,2% SDS at 60° C. for 10 minutes. Hybridization signals were recorded with a Fujix BAS 2000 phosphoimager. The data were analyzed using MacBAS (ver. 2.1) software. The hybridization signal was quantitated and adjusted for probe specific activity and length. The hybridization signal for each sample was also adjusted for loading by virtue of hybridization to a tubulin cDNA probe (Marks et al., 1987). In this manner, both the quantitative and temporal accumulation of the KNAT411 gene was determined and compared to that of the well characterized seed-specific Arabidopsis 12S gene.

Figure 3:
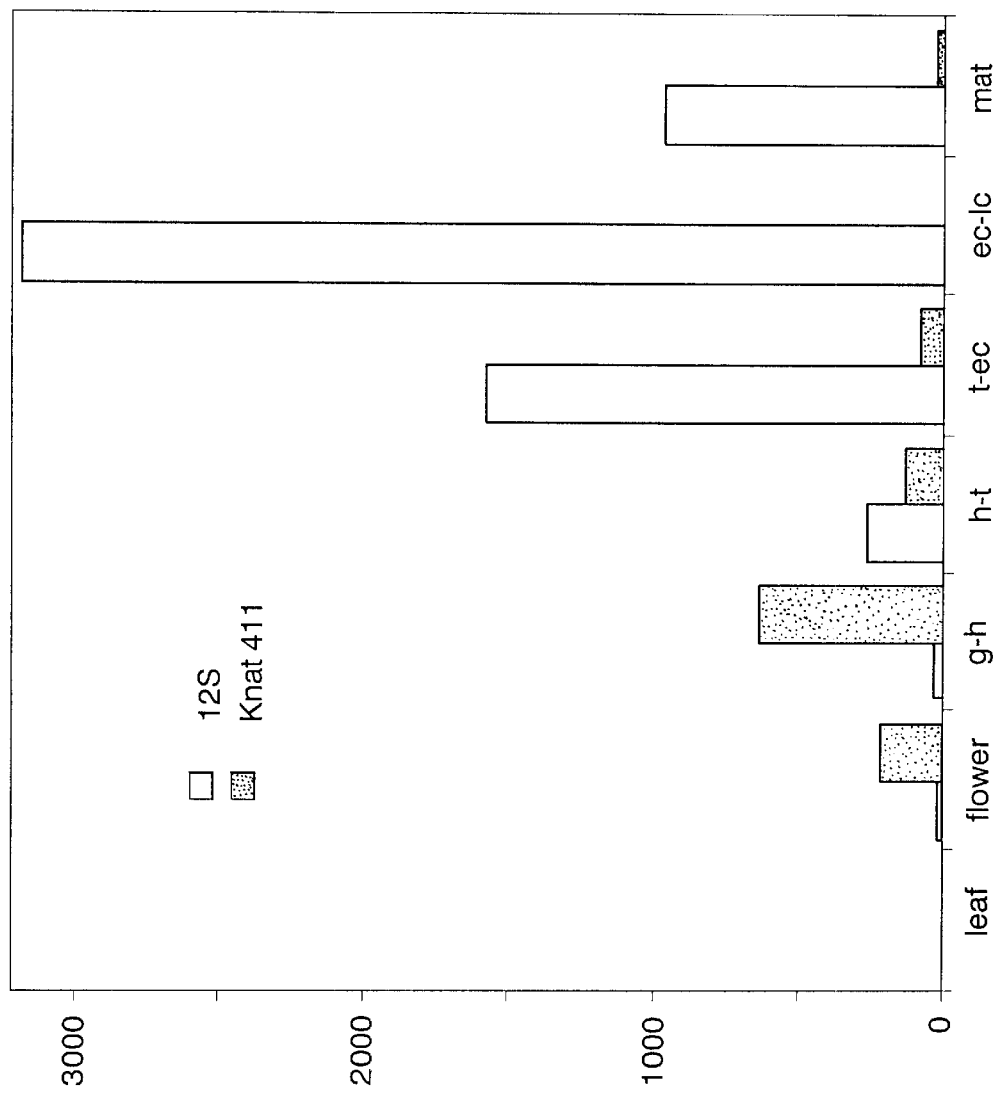
FIG. 3 graphically depicts the developmental profile of KNAT411 and 12S seed storage protein gene expression in different tissues of Arabidopsis.

FIG. 3 shows the developmental accumulation of KNAT411 transcripts vs Arabidopsis 12S albumin seed storage gene during seed development. As shown in FIG. 3, KNAT411 is expressed early in seed development with expression detected in flowers and which expression peaks in globular to heart stage siliques (g-h). Expression declines in heart to torpedo stage siliques (h-t) and is not detected at the later stage of early cotyledon to late cotyledon stage siliques (ec-ic). A low level of KNAT411 was detected in mature seeds.

EXAMPLE 3

CHARACTERIZATION OF KNAT411 BY IN SITU HYBRIDIZATION

In situ hybridization analysis was used to establish the spatial accumulation of mRNA for the KNAT411 gene. This approach utilized a digoxygenin-labeled RNA probe which was detected with an antibody conjugated to alkaline phosphatase. It was determined that this was the most reliable method to detect gene expression at the cellular level in developing Arabidopsis seeds.

Tissue representing developing Arabidopsis seeds and germinating seedlings was collected and fixed in a solution containing 4% formaldehyde and 0.5% glutaraldehyde in 100 mM phosphate buffer (pH 7.0) at 0° C. overnight. The tissue was dehydrated in 10%, 30%, 50%, 70%, 85%, 95%, and 100% ethanol three times for thirty minutes at room temperature for each step. The solvent was gradually changed to xylenes in the following series 25%, 50%, 75% and 100% three times at room temperature. An equal amount of Paraplast (Sigma, St. Louis, Mo.) was added to the xylenes and incubated overnight at room temperature. The mixture was then placed at 42° for 6 hours. It was decanted off, replaced with 100% molten paraplast and placed at 60° C. The paraplast was replaced four times at four hour intervals to remove all the xylenes. The paraplast embedded tissue was then poured into molds and cooled to room temperature. The embedded tissue was kept in a desiccated container at room temperature until sectioning.

Tissue was sectioned into 8 $\mu$m ribbons with a Lipshaw Model 50A microtome. The ribbons were overlayed on DEPC treated $H_2O$ on poly-L lysine coated microscope slides on a 45° C. slide warmer. The water evaporated overnight, fixing the sections to the slides. The slides were stored at room temperature.

The digoxygenin labeled riboprobes were prepared with the Genius™ 4 nonradioactive RNA in vitro transcription kit (Boehringer Mannheim, Indianapolis, Ind.). The cDNA encoding the KNAT411 gene was cloned into pBluescript (SK) as a EcoRI/XhoI fragment. The template for antisense riboprobe was generated by an EcoRI digest, gel purified and quantitated. To generate the template for sense strand riboprobes, the KNAT411 cDNA was excised from pBluescript (SK) as an EcoRI fragment and cloned into pBluescript (KS) as the same. An anti-sense GUS riboprobe was generated and used as a negative control. The GUS coding region was cloned into pBluescript (KS) as a BamHI/SacI fragment. The template for antisense riboprobe was generated by a BamHI digest, gel purified and quantitated. Each riboprobe was synthesized in a reaction containing 2 $\mu$g linearized DNA template, 2 $\mu$l 10×T7 RNA polymerase buffer, 2 $\mu$l 10×NTPs containing digoxygenin-UTP, 1 $\mu$l RNAse inhibitor and 2 $\mu$l T7 RNA polymerase (5U) in a 20 $\mu$l reaction. The reaction was incubated at 37° C. for 2 hours. The DNA template was digested with 5 Units of RNAse-free DNAse (Boehringer Mannheim, Indianapolis, Ind.) for 5 minutes at 37° C. The digoxygenin-labeled riboprobe was then purified over a G-50 spin column (Boehringer Mannheim, Indianapolis, Ind.) and ethanol precipitated.

Each riboprobe was sheared into strands averaging 100–200 bases by alkali treatment. RNA pellets were dissolved in 22 $\mu$l DEPC treated $H_2O$. Only 20 $\mu$l of the redissolved riboprobe was sheared with the addition of 20 $\mu$l 120 mM $Na_2CO_3$, 80 mM $NaHCO_3$ and incubating at 65° C. for 35 minutes. The reaction was terminated with the addition of 40 $\mu$l sodium acetate and the riboprobe was ethanol precipitated. The remaining riboprobe was reserved for gel analysis. Each riboprobe was resuspended in DEPC $H_2O$, quantitated and analyzed by gel electrophoresis. The riboprobes were kept at −90° C. until use.

The slides were prepared for hybridization first by removing the paraplast by immersion in 100% xylenes twice for 10 minutes each. The slides were transferred to 1:1 xylenes:ethanol for five minutes followed by 100% ethanol for two changes of 10 minutes each to remove the xylenes. The slides were then rehydrated through a series (dd$H_2O$:ethanol) of 5%, 15%, 30%, 50%, 70%, 85% and 95% dd$H_2O$ for five minutes each step. The slides were finally transferred to PBS (50 mM phosphate buffer(pH 7.0), 130 mM NaCl in DEPC $H_2O$ for two 5 minute incubations at room temperature. The slides were then incubated in 50 mM phosphate buffer (pH 7.0) containing 100 $\mu$g/ml proteinase K for 15 minutes at 37° C.

The digests were stopped by two washes in PBS for five minutes each.

The tissue was then acetylated by incubation in fresh 1% triethanolamine (pH 8.0), 0.5% acetic anhydride for 10 minutes at room temperature. The reaction was terminated by two washes in PBS for 5 minutes each. This was followed by a quick dehydration series in 5%, 15%, 30%, 50%, 70%, 85%, 95%, and two times 100% ethanol. The slides were air dried and kept at room temperature until the hybridization.

Each riboprobe was diluted to 300 ng/ml in hybridization solution containing 50% deionized formamide, 300 mM NaCl, 10 mM Tris-HCl(pH 7.5), 5 mM EDTA (pH 8.0), 1×Dendhart's solution, 10% dextran sulfate, 1 mg/ml yeast tRNA and 500 $\mu$g/ml poly-A RNA. The hybridization mixture was overlayed on each dried slide (250 $\mu$l per slide), covered with a coverslip, and incubated overnight in a moist container at 50° C.

The unhybridized probe was removed by washing the slides in 2×SSC/50% deionized formamide 4 times for 30 minutes each at 50° C. The slides were then washed in NTE buffer (500 mM NaCl, 10 mM Tris-HCl (pH 7.5), 1 mM EDTA (pH 8.0)) twice at 37° C. for 10 minutes each. The slides were then treated with 20 U/ml RNAse A plus 20 $\mu$g/ml RNAse T1 in NTE buffer for 30 minutes at 37° C. The RNAse cocktail was removed by 4 washes in NTE buffer at 37° C. for 30 minutes each. The slides were washed in 2×SSC/50% deionized formamide at 50° C. for 30 minutes and then washed in PBS at room temperature twice for 10 minutes each.

The slides were then incubated in Buffer I (100 mM Tris-HCl (pH 7.5), 150 mM NaCl) for 30 minutes at room temperature. The slides were blocked in Buffer I containing 1% BSA or gelatin at room temperature for 30 minutes. An anti-digoxigenin Fab fragment conjugated with alkaline phosphatase (Boehringer Mannheim) was diluted 1:2500 in Buffer I containing 1% BSA or gelatin and 500 $\mu$l was added to each slide. The slides were covered with cover slips and incubated at room temperature for one hour. The unhybridized antibody was removed with 4 washes in Buffer I at room temperature for 15 minutes each. The slides were rinsed in Buffer III (100 mM Tris-HCl (pH 9.5), 100 mM NaCl, 50 MM $MgCl_2$) for two minutes at room temperature and incubated in color solution to detect hybridization. The color solution contained 337.5 µg/ml NBT (nitroblue tetrazolium) and 175 µg/ml X-phosphate (5-bromo-4-chloro-3-indolyl phosphate) in Buffer III. The color reaction was carried out for 2 hours to 3 days, depending on the experiment.

The color reactions were stopped by washing slides in deionized $H_2O$. The slides were dehydrated quickly in 30%, 50%, 70%, 85%, 95% and 100% ethanol and air dried. The samples were preserved in several drops of either Euparal (BioQuip Products, Inc., Gardena, Calif.) or Permount (Fisher, Fair Lawn, N.J.) and a cover glass was mounted. The mounted samples were dried for several days at room temperature. Micrographs of individual sections were taken with a Zeiss Axiophot microscope using DIC optics.

The in situ hybridization data is presented in FIGS. 2A through 2D. The KNAT411 mRNA is detected as early as the octant stage. The transcripts of KNAT411 accumulates gradually through late heart stage and decreases rapidly afterward. Limited KNAT411 hybridization was detected in provascular tissue of torpedo stage embryos, and no apparent expression was detected during maturation.

EXAMPLE 4

KNAT411 GENE ORGANIZATION

Genomic Clone Isolation

Genomic DNA was prepared from Arabidopsis (cv. Landsberg) according to Taylor et al. (1993) *Methods in Plant Molecular Biology and Plant Biotechnology*, Boca Raton, Fla.: CRC Press; 37–47. The DNA was partially digested with MboI and overlayed on a sucrose gradient for size selection (Ausubel et al., 1994). Fractions containing DNA fragments ranging from 15–25 Kb were combined and precipitated. The DNA was dissolved in TE buffer, quantitated and ligated to lambda pGEM-11 XhoI half-site arms according to manufactures' instructions (Promega, Madison, Wis.). The DNA was packaged using Gigapack Gold packaging extracts (Stratagene, La Jolla, Calif.) and plated on KW251 cells. Characterization of this library revealed a 1% background and an average insert size of 20 Kb. The library contained approximately $1.5 \times 10^6$ plaque forming units and was amplified and stored in SM buffer containing $CHCl_3$ at 4° C.

Approximately 25,000 pfu of this library was plated on KW251 cells. Plaques were transferred to nitrocellulose membranes as recommended by the manufacturer and hybridized by standard methods (Ausubel et al., 1994). After 4 hours of prehybridization in hybridization II buffer (1% crystalline BSA, 1 mM EDTA, 0.5 M $NAHPO_4$, pH 7.2 7% SDS) at 65° C, the random-primed DNA generated from the KNAT411 cDNA template, which had been boiled in 50% formamide for 3 minutes, was added to the same hybridization solution. Hybridization was continued up to 24 hours at 65° C. The filters were washed twice in 0.5% crystalline BSA, 1 mM EDTA, 40 mM $NaHPO_4$, pH 7.2, 5% SDS for 5 minutes each at room temperature, and then three times in 1 mM EDTA, 40 mM $NaHPO_4$, pH 7.2, 1% SDS for 10 minutes each at 65° C. Autoradiographs were exposed for 1 day at –95° C.

Several phage which hybridized to the KNAT411 were plaque purified. Phage DNA was prepared using the liquid lysate protocol (Ausubel et al. 1994) and aliquots were digested with BamHI, EcoRI, HindIII, SacI, and XbaI separately or in combination (double digestion). A 3.2 kb HindIII/SacI fragment was identified by DNA gel blot analysis using KNAT411 cDNA fragment as a probe. This fragment was subsequently cloned into pBluescript (KS) at the corresponding sites. Sequence analysis revealed that this 3.2 kb HindIII/SacI fragment contains 200 bp of the KNAT411 5' coding region and 3 kb of the upstream region.

Southern Analysis

Arabidopsis genomic DNA was isolated from whole plants according to the CTAB (hexadecyltrimethylammonium bromide plant genomic DNA preparation protocol (Taylor et al., 1993). Genomic DNA (10 µg) was digested in the presence of excess enzyme activity at 37° C. overnight and then resolved on a 0.7% agarose gel. Separate digestions using BamHi, EcoRI, HindIII, SacI and XbaI were performed on the genomic DNA. DNA was transferred by blotting to Hybond-N$^{+TM}$ membrane (Amersham) with 0.1 N NaOH. Southern hybridizations were performed essentially as described for the genomic clone isolation. After 4 hours prehybridization in hybridization II buffer (1% crystalline BSA, 1 mM EDTA, 0.5 M $NaHPO_4$, pH 7.2, 7% SDS) at the hybridization temperature, the random-primed DNA probe generated from the KNAT411 cDNA template, which had been denatured for ten minutes in boiling water, was added to the same hybridization solution. Hybridization was continued up to 24 hours. The filters were washed twice in 0.5% crystalline BSA, 1 mM EDTA, 40 mM $NaHPO_4$, pH 7.2, 5% SDS for 5 minutes each at room temperature, and then, stringently, three times in 1 mM EDTA, 40 mM $NaHPO_4$, pH 7.2, 1% SDS for 10 minutes each at high temperature. The high stringency hybridizations were performed at 68° C. and the stringent washing steps were done at the same temperature. The low stringency hybridizations were done at 50° C. and the stringent washing steps were done at 60° C.

Figure 8A:
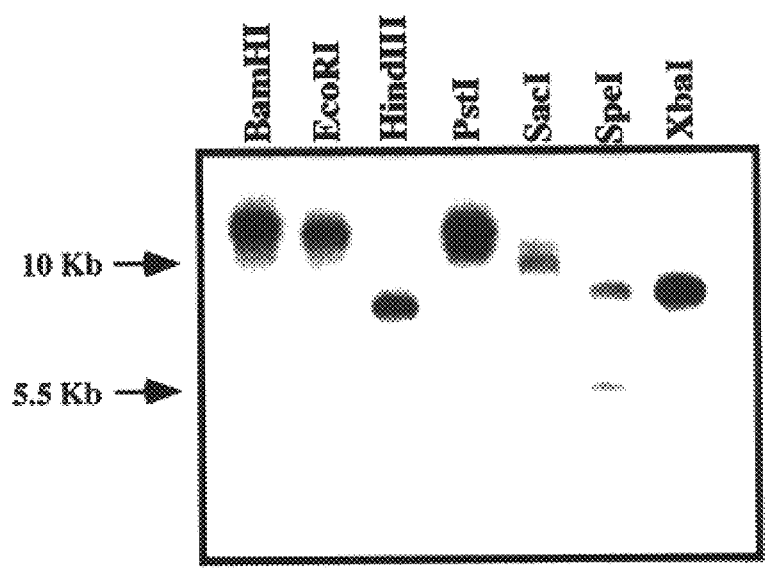
FIG. 8A is a genomic DNA blot analysis of different restriction enzyme digested *Arabidopsis thaliana* DNA. The full length KNAT411 cDNA probe detected a single band in most of the restriction enzyme digests under high stringency hybridization conditions.
Figure 8B:
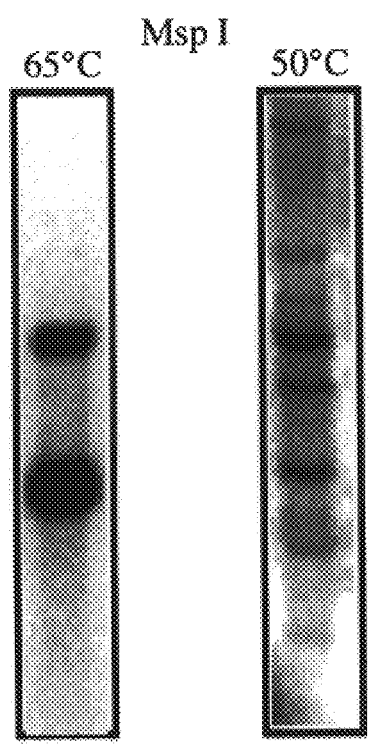
FIG. 8B is a genomic DNA blot analysis of MspI digested genomic Arabidopsis DNA under high stringency (65° C.) and low stringency (50° C.) hybridization conditions.

The KNAT411 cDNA probe gave single hybridization signals in most of the restriction enzyme digestion when DNA gel blot analysis was performed under high stringency conditions, indicating that it is present as a single copy gene in the Arabidopsis genome (FIG. 8). Under reduced stringency conditions, the KNAT411 cDNA probe recognized several additional bands, indicating the presence of a larger number of knotted-like or KNAT411-like sequences in the Arabidopsis genome.

Genomic sequences of KNAT411 were obtained by sequencing a 3 kb PCR fragment amplified from wild type Arabidopsis genomic DNA using a pair of primers (411-5' CAT ACG AAC ACA ATC T) and 411-3' (AAT GAA TGA TCA CAC C) primers) located at the 5'-and 3' ends of the cDNA clone. The amplified genomic fragment was cloned into a PCR cloning vector pT7Blue (Novagen, Madison, Wis.). The genomic organization of KNAT411 was defined by comparing genomic and cDNA sequences. KNAT411 contains five exons separated by four introns. The fourth intron interrupts the homeodomain near the N-terminal end of the second helix. This intron position is conserved in all the knotted genes (Kerstetter et al. 1994). A small third intron located inside the ELK domain is also conserved among all the class II members (Kerstetter et al., 1994).

DNA Sequencing and Sequence Analysis mini-prep plasmid DNA was used as templates in cycle sequencing reactions with the SequiTherm cycle sequencing kit (Epicenter Technologies, Madison, Wis.) or the ABI PRISM™ dye terminator cycle sequencing kit (Perkin Elmer, Foster City, Calif.). Sequence analysis was done locally with GCG (Devereux et al., 1984) on a DEC MicroVAXII; database searches were done remotely through NCBI using the BLAST algorithm (Altschul et al. (1990) *J. Mol. Biol.*, 215; 403–410).

Genomic and cDNA sequence data for the gene was aligned using Geneworks, Version 2.3 software (Intelligenetics, Mountain View, Calif.). Introns were initially located with a DNA dot matrix algorithm. The longest open reading frame found in the KNAT411 cDNA was considered to be the coding sequence and the codon for that methionine residue was labeled +1. The coding sequence was translated from that residue.

The genomic clone contained 3 Kb of the KNAT411 upstream regulatory sequences and 200 bp of the KNAT411 5' coding region. The KNAT411 cDNA clone contains 120 nucleotides of 3' untranslated sequences before the polyA tail. A putative polyadenylation signal (aataa) is present 19 nucleotides upstream of the polyA tail.

A promoter fragment of 1,679 bp lies immediately upstream of the putative translational start site of KNAT411 and was amplified by PCR. The sequence of the promoter fragment is provided in FIG. 4A. The putative TATA box, CAT box sequences and the first ATG are bolded in FIG. 4A. The corresponding primer sequences used to amplify the promoter fragment are underlined. A Hind III site and a Bam HI site were introduced at the 5' end and 3' end of the promoter during PCR to facilitate subsequent cloning.

EXAMPLE 5

HETEROLOGOUS GENE EXPRESSION UNDER CONTROL OF THE KNAT411 PROMOTER

Construction of Promoter-GUS Expression Vector

Figure 4B:
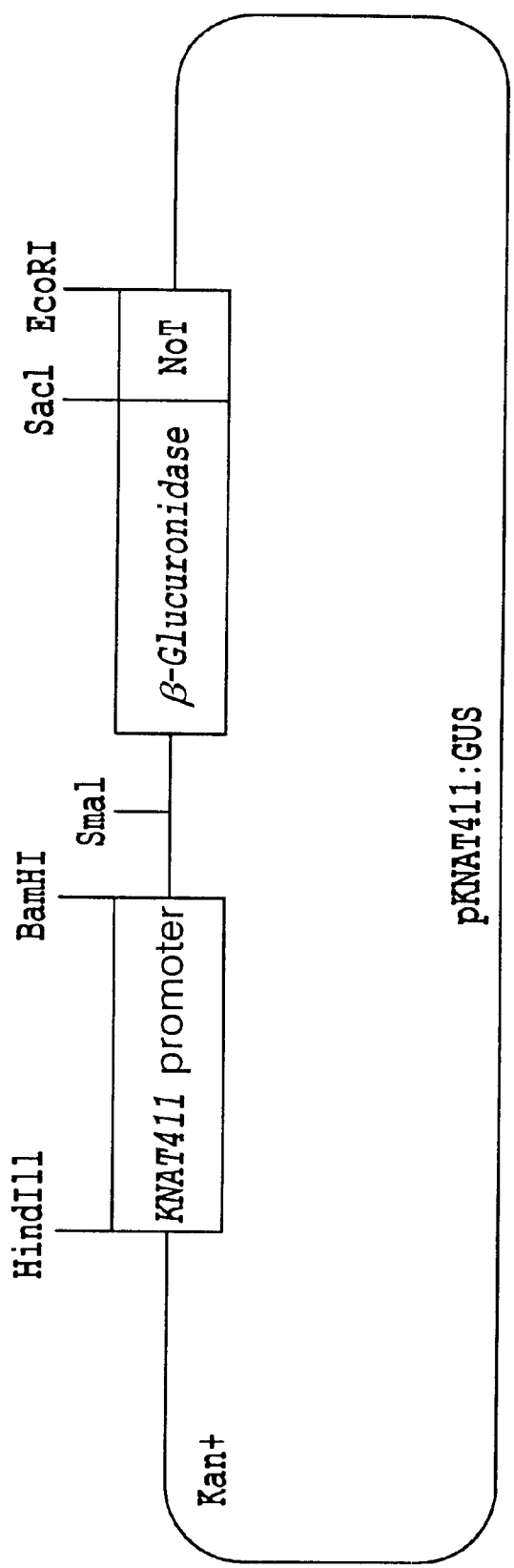
FIG. 4B illustrates the KNAT411 promoter/GUS expression vector.
Figure 5A:
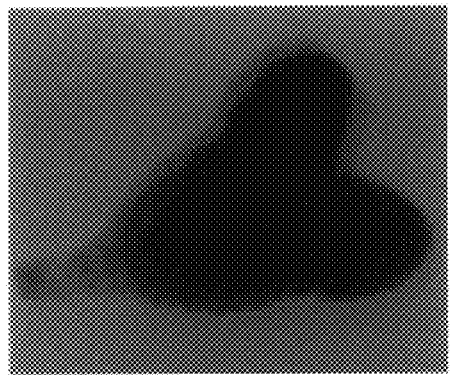
FIG. 5 is a photomicrograph of developing transgenic Arabidopsis embryos showing histochemical localization of GUS gene expression driven by the KNATA411 promoter.
Figure 5B:
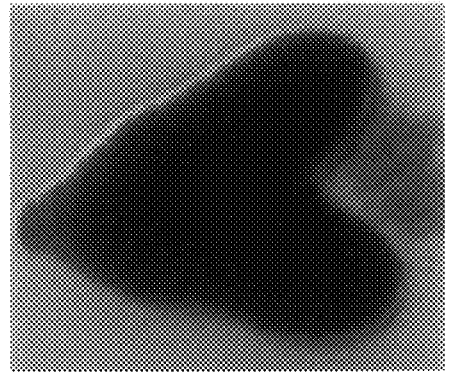
Figure 5C:
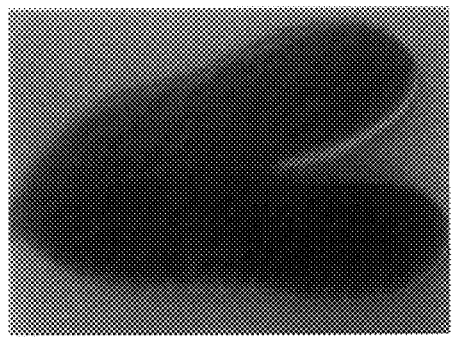
Figure 5D:
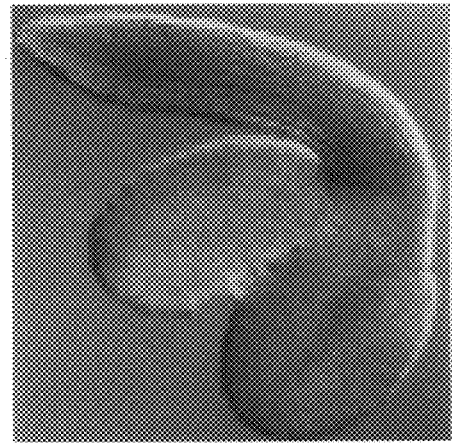

An expression cassette based on the KNAT411 gene was constructed. The 1,679 bp promoter fragment which lies immediately upstream of the putative translational start site of KNAT411 gene was amplified by PCR. This amplified fragment was cloned into the pBI121 vector (Bevan, M.,1984 *Nucl. Acids Res.* 12:8711–8721) by replacing the 35S promoter at the corresponding HindIII and BamHI site to create a translational fusion with the GUS reporter gene. The resultant plasmid, designated pKNAT411:GUS, is illustrated in FIG. 4B.

Transformation of Plants with Promoter-GUS Fusions

The KNAT411/GUS expression construct was used to transform *Arabidopsis thaliana* (cvs. Landsberg erecta or Columbia) according to standard procedures (Bechtold et al., 1993; Horsch et al., 1985; Nunberg et al., 1994; Valvekens et al. (1988) *Proc. Natl. Acad. Sci. USA*, 85; 5536–5540). Constructs were transferred into either the LBA4404 or the GV3101 Agrobacterium tumefaciens strains. Constructs were then transformed into Arabidopsis using either root transformation (Valvekens et al., 1988) or vacuum infiltration (Bechtold et al., 1993). Positive Arabidopsis transformants were selected on media containing 50 µg/ml kanamycin and 600 µg/ml carbenicillin. Regenerated plants were transferred to soil. Plants were self-pollinated, and seeds were regenerated on 50 µg/ml kanamycin and 600 µg/ml carbenicillin (Arabidopsis). The copy number of each GUS construction integrated into the plant genome was determined by genomic DNA gel blot analysis. GUS activity was analyzed in R2 progeny.

Biochemical and Histochemical Detection of GS Activity

The standard procedures of Jefferson (1987a) and Jefferson et al. (1987b) as detailed in Bogue et al. (1990) and Nunberg et al. (1994) were followed. Biochemical assays were performed by mixing plant tissue lysates with an equal volume of 2 mM 4-methylumbelliferyl β-D-glucuronide and incubating for 1 hour at 37° C. Fluorometric analyses were done with a minifluorometer (model TKO-100; Hoefer Scientific Instruments, San Francisco, Calif.) as described previously (Jefferson, 1987a). Protein concentrations were determined by the method of Bradford (1976). Histochemical localizations for GUS activity were determined by incubating whole tissue in 1 mM 5-bromo-4-chloro-3-indolyl glucuronide (X-gluc) as described by Jefferson (1987a) and Jefferson et al. (1987b). The reactions described here were done in the presence of 1 mM potassium ferricyanide and 1 mM potassium ferrocyanide. The X-gluc treatment was carried out for 12 to 24 hours at 37° C. For gross analysis, the siliques were sectioned and examined under the microscope (100X magnification). As FIG. 5 demonstrates, several early embryos (prior to the heart stage) exhibit GUS staining.

Figure 6A:
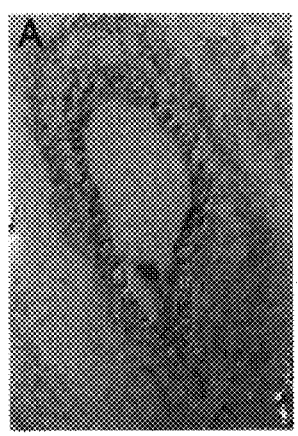
FIGS. 6A–6C are photomicrographs of transgenic Arabidopsis preglobular stage embryos showing histochemical localization of GUS gene expression driven by the KNAT411 promoter.
Figure 6B:
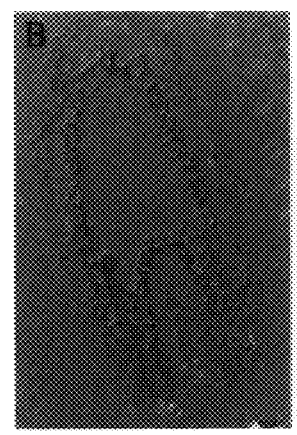
Figure 6C:
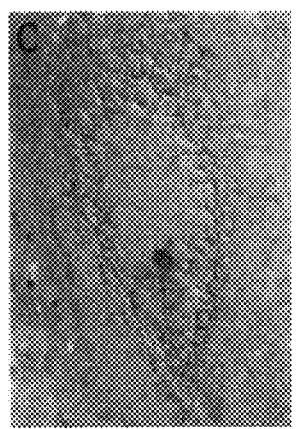
Figure 6D:
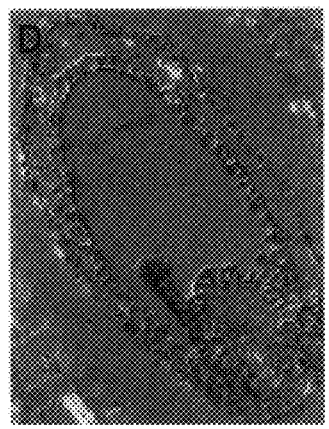
FIGS. 6D and 6E are photomicrographs of transgenic Arabidopsis globular stage embryos showing histochemical localization of GUS gene expression driven by the KVAT411 promoter.
Figure 6E:
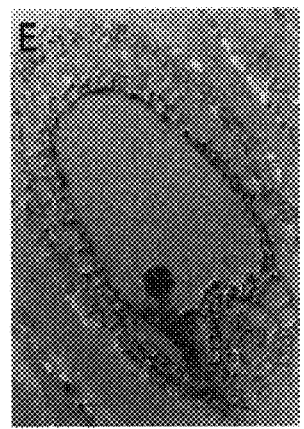
Figure 6F:
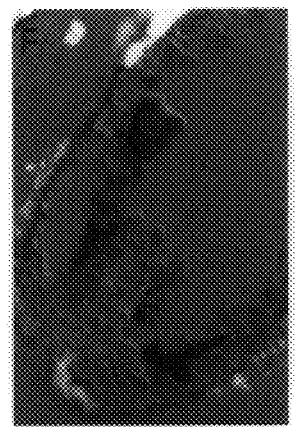
FIG. 6F is a photomicrograph of a heart stage embryo from a transgenic Arabidopsis heart stage embryo showing histochemical localization of GUS gene expression driven by the KNAT411 promoter.

For fine analysis, stained siliques were embedded in paraplast, sectioned (10 micron thickness), xylene and ethanol treated prior to observation by microscope. Tissue sections were visualized by photomicrography using Kodak Ektachrome 160 ASA tungsten film. As shown in FIG. 6, GUS gene expression is under control of the KNAT411 promoter as early as preglobular stage embryos (FIG. 6A–6C). GUS expression continues under control of the KNAT411 promoter through the globular stage embryo (FIGS. 6D and 6E) and heart stage embryo (FIG. 6F).

What is claimed is:

1. An isolated nucleic acid comprising a promoter which has the seed-specific promoter activity of the KNAT411 promoter, said promoter hybridizing under stringent hybridization conditions to the KNAT411 promoter having the nucleotide sequence as set forth in SEQ ID NO:1, wherein said stringent hybridization conditions comprise hybridization in 4×SSC at 65° C. and washing in 0.1×SSC at 65° C.

2. An isolated nucleic acid comprising a promoter which has the seed-specific promoter activity of the KNAT411 promoter, said promoter having a sequence identity of about 60% to about 65% when compared to the nucleotide sequence of the KNAT411 promoter as set forth in SEQ ID NO:1.

3. An isolated nucleic acid comprising a promoter which has the seed-specific promoter activity of the KNAT411 promoter, said promoter having a sequence identity of about 65% to about 75% when compared to the nucleotide sequence of the KNAT411 promoter as set forth in SEQ ID NO:1.

4. An isolated nucleic acid comprising a promoter which has the seed-specific promoter activity of the KNAT411 promoter, said promoter having a sequence identity of about 75% to about 85% when compared to the nucleotide sequence of the KNAT411 promoter as set forth in SEQ ID NO:1.

5. An isolated nucleic acid comprising a promoter which has the seed-specific promoter activity of the KNAT411 promoter, said promoter having a sequence identity of about 85% to about 90% when compared to the nucleotide sequence of the KNAT411 promoter as set forth in SEQ ID NO:1.

6. An isolated nucleic acid comprising a promoter which has the seed-specific promoter activity of the KNAT411 promoter, said promoter having a sequence identity of about 90% or greater when compared to the nucleotide sequence of the KNAT411 promoter as set forth in SEQ ID NO:1.

7. An isolated nucleic acid comprising a KNAT411 promoter which directs seed-specific expression beginning in the early embryo, said promoter having the nucleotide sequence set forth in SEQ ID NO:1.

8. A plant transformation vector which comprises the nucleic acid of any one of claims 1, 2, 3, 4, 5, 6 or 7.

9. A plant cell comprising the nucleic acid of any one of claims 1, 2, 3, 4, 5, 6 or 7, said nucleic acid being non-native to said plant cell.

10. A plant cell comprising the plant transformation vector of claim 8.

11. A plant which has been regenerated from the plant cell of claim 9.

12. A plant which has been regenerated from the plant cell of claim 10.

13. The plant cell of claim 9 wherein said plant is at least one of a sunflower, soybean, maize, cotton, tobacco, peanut, flax, Arabidopisis, oil seed rape or other Brassica plant.

14. The plant of claim 10 wherein said plant is at least one of a sunflower, soybean, maize, cotton, tobacco, peanut, flax, Arabidopisis, oil seed rape or other Brassica plant.

15. An expression cassette which comprises the promoter of any one of claims 1, 2, 3, 4, 5, 6 or 7, said promoter operably linked to at least one of a nucleic acid encoding a heterologous gene or a nucleic acid encoding a sequence complementary to a native plant gene.

16. An expression cassette which comprises the promoter of any one of claims 1, 2, 3, 4, 5, 6 or 7, said promoter operably linked to a recombinase gene, said recombinase gene selected from the group consisting of Cre, FLP, R and Gin.

17. The expression cassette of claim 15 wherein the heterologous gene is at least one of a fatty acid synthesis gene or a lipid metabolism gene.

18. The expression cassette of claim 15, wherein the heterologous gene is selected from the group consisting of an acetyl-coA carboxylase gene, a ketoacyl synthase gene, a malonyl transacylase gene, a lipid desaturase gene, an acyl carrier protein (ACP) gene, a thioesterase gene, an acetyl transacylase gene, and an elongase gene.

19. The expression cassette of claim 18 wherein the lipid desaturase gene is selected from the group consisting of a Δ6-desaturase gene, a Δ12-desaturase gene, and a Δ15-desaturase gene.

20. An expression vector which comprises the expression cassette claim 15.

21. An expression vector which comprises the expression cassette of claim 16.

22. An expression vector which comprises the expression cassette of claim 17.

23. An expression vector which comprises the expression cassette of claim 18.

24. An expression vector which comprises the expression cassette of claim 19.

25. A cell comprising the expression cassette of claim 15.

26. A cell comprising the expression cassette of claim 16.

27. A cell comprising the expression cassette of claim 17.

28. A cell comprising the expression cassette of claim 18.

29. A cell comprising the expression vector of claim 19.

30. The cell of claim 25 wherein said cell is a bacterial cell or a plant cell.

31. The cell of claim 26 wherein said cell is a bacterial cell or a plant cell.

32. The cell of claim 27 wherein said cell is a bacterial cell or a plant cell.

33. The cell of claim 28 wherein said cell is a bacterial cell or a plant cell.

34. The cell of claim 29 wherein said cell is a bacterial cell or a plant cell.

35. A transgenic plant comprising the expression cassette of claim 15.

36. A transgenic plant comprising the expression cassette of claim 16.

37. A transgenic plant comprising the expression cassette of claim 17.

38. A transgenic plant comprising the expression cassette of claim 18.

39. A plant which has been regenerated from the plant cell of claim 30.

40. A plant which has been regenerated from the plant cell of claim 31.

41. A plant which has been regenerated from the plant cell of claim 32.

42. A plant which has been regenerated from the plant cell of claim 33.

43. A plant which has been regenerated from the plant cell of claim 34.

44. The plant of claim 39 wherein said plant is at least one of a sunflower, soybean, maize, cotton, tobacco, peanut, flax, Arabidopisis, oil seed rape or other Brassica plant.

45. The plant of claim 40 wherein said plant is at least one of a sunflower, soybean, maize, cotton, tobacco, peanut, flax, Arabidopisis, oil seed rape or other Brassica plant.

46. The plant of claim 41 wherein said plant is at least one of a sunflower, soybean, maize, cotton, tobacco, peanut, flax, Arabidopisis, oil seed rape or other Brassica plant.

47. The plant of claim 42 wherein said plant is at least one of a sunflower, soybean, maize, cotton, tobacco, peanut, flax, Arabidopisis, oil seed rape or other Brassica plant.

48. The plant of claim 43 wherein said plant is at least one of a sunflower, soybean, maize, cotton, tobacco, peanut, flax, Arabidopisis, oil seed rape or other Brassica plant.

49. Progeny of the plant of claim 35 wherein said progeny contains said expression cassette.

50. Progeny of the plant of claim 36 wherein said progeny contains said expression cassette.

51. Progeny of the plant of claim 37 wherein said progeny contains said expression cassette.

52. Progeny of the plant of claim 38 wherein said progeny contains said expression cassette.

53. Seed from the plant of claim 35.

54. Seed from the plant of claim 36.

55. Seed from the plant of claim 37.

56. Seed from the plant of claim 38.

57. A method for directing seed-specific expression of a gene or a sequence complementary to a native plant gene in a plant, said method comprising introducing into a plant cell an isolated nucleic acid comprising a KNAT411 promoter having the nucleotide sequence as set forth in SEQ ID NO:1 or a promoter which has the seed-specific promoter activity of said KNAT411 promoter and hybridizes to said KNAT411 promoter under stringency conditions comprising hybridization in 4×SSC at 65° C. and washing in 0.1×SSC at 65° C., said KNAT411 promoter or the promoter which hybridizes to said KNAT411 promoter being operably linked to said gene or sequence complementary to a native plant gene, and regenerating a plant from said plant cell in order to effect seed-specific expression of said gene or sequence complementary to a native plant gene.

58. A method for activating a site-specific recombination system in the early embryo of a seed, said method comprising introducing into a plant cell an isolated nucleic acid comprising a KNAT411 promoter having the nucleotide sequence as set forth in SEQ ID NO:1 or a promoter which has the seed-specific promoter activity of said KNAT411 promoter and which hybridizes to said KNAT411 promoter under stringency conditions comprising hybridization in 4×SSC at 65° C. and washing in 0.1×SSC at 65° C., said KNAT411 promoter or the promoter which hybridizes to said KNAT411 promoter being operably linked to a recombinase gene selected from the group consisting of Cre, FLP, R or Gin, and regenerating a plant from said plant cell in order to activate site-specific recombination in the early embryo of a seed.

59. Progeny of the plant of claim 11, wherein said progeny comprises said nucleic acid.

60. Progeny of the plant of claim 12, wherein said progeny comprises said plant transformation vector.

\* \* \* \* \*